United States Patent
Shao et al.

(10) Patent No.: US 7,907,698 B2
(45) Date of Patent: Mar. 15, 2011

(54) GATED CT WITH IRREGULAR SAMPLING FOR SLOW CT ACQUISITION

(75) Inventors: Lingxiong Shao, Saratoga, CA (US); Jinghan Ye, Fremont, CA (US); Ron Koops, Castro Valley, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 71 days.

(21) Appl. No.: 12/375,426

(22) PCT Filed: Jul. 18, 2007

(86) PCT No.: PCT/US2007/073734
§ 371 (c)(1),
(2), (4) Date: Jan. 28, 2009

(87) PCT Pub. No.: WO2008/079444
PCT Pub. Date: Jul. 3, 2008

(65) Prior Publication Data
US 2009/0225933 A1    Sep. 10, 2009

Related U.S. Application Data

(60) Provisional application No. 60/820,809, filed on Jul. 31, 2006.

(51) Int. Cl.
*G01N 23/083* (2006.01)
*H05G 1/62* (2006.01)
(52) U.S. Cl. .................................. 378/8; 378/15; 378/63
(58) Field of Classification Search .................. 378/4, 8, 378/15, 63, 95
See application file for complete search history.

(56) References Cited

U.S. PATENT DOCUMENTS

| | | | | |
|---|---|---|---|---|
| 6,134,292 | A | * | 10/2000 | Hsieh ................................. 378/4 |
| 6,411,670 | B1 | * | 6/2002 | Besson .............................. 378/4 |
| 6,670,614 | B1 | | 12/2003 | Plut et al. |
| 6,878,941 | B2 | | 4/2005 | Balan et al. |

(Continued)

FOREIGN PATENT DOCUMENTS

EP    1420269 A1    5/2004

OTHER PUBLICATIONS

Lagerwaard, F. J., et al.; Multiple "Slow" CT Scans for Incorporating Lung Tumor Mobility in Radiotherapy Planning; 2001; Int. J. Radiation Oncology Biol. Phys.; 51(4)932-937.

(Continued)

*Primary Examiner* — Edward J Glick
*Assistant Examiner* — Thomas R Artman

(57) ABSTRACT

A physiological parameter monitor (44) monitors a cyclic physiological parameter and generates a cyclic parameter phase indicative signal. A radiation system (8) is disposed adjacent an examination region (18, 28) to generate transmission radiation data and emission radiation data. First and second sorting devices (48, 74) sort corresponding transmission and emission radiation data into transmission radiation data sets (50) and emission radiation data sets (78) corresponding to each of a plurality of the cyclic parameter phases. A data processor (60) reconstructs attenuation maps (62) from the transmission data for each of the plurality of cyclic parameter phases. An image processor (80) corrects the emission radiation data of each cyclic parameter phase with the attenuation map (62) of the same cyclic parameter phase and reconstructs the attenuation corrected emission data sets into an image representation for each cyclic parameter phase.

21 Claims, 2 Drawing Sheets

U.S. PATENT DOCUMENTS

| | | | |
|---|---|---|---|
| 6,879,656 B2* | 4/2005 | Cesmeli et al. | 378/4 |
| 7,251,308 B2* | 7/2007 | Tsuyuki | 378/8 |
| 7,332,724 B2* | 2/2008 | Hefetz et al. | 250/370.06 |
| 7,409,033 B2* | 8/2008 | Zhu et al. | 378/4 |
| 2003/0007593 A1* | 1/2003 | Heuscher et al. | 378/4 |
| 2003/0128801 A1* | 7/2003 | Eisenberg et al. | 378/19 |
| 2004/0077941 A1* | 4/2004 | Reddy et al. | 600/428 |
| 2004/0120452 A1* | 6/2004 | Shapiro et al. | 378/19 |
| 2006/0050845 A1 | 3/2006 | Juni | |
| 2006/0050847 A1 | 3/2006 | Jaffray et al. | |

OTHER PUBLICATIONS

Nehmeh, S. A., et al.; Four-dimensional (4D) PCT/CT imaging of the thorax; 2004; Med. Phys.; 31(12)3179-3186.

* cited by examiner

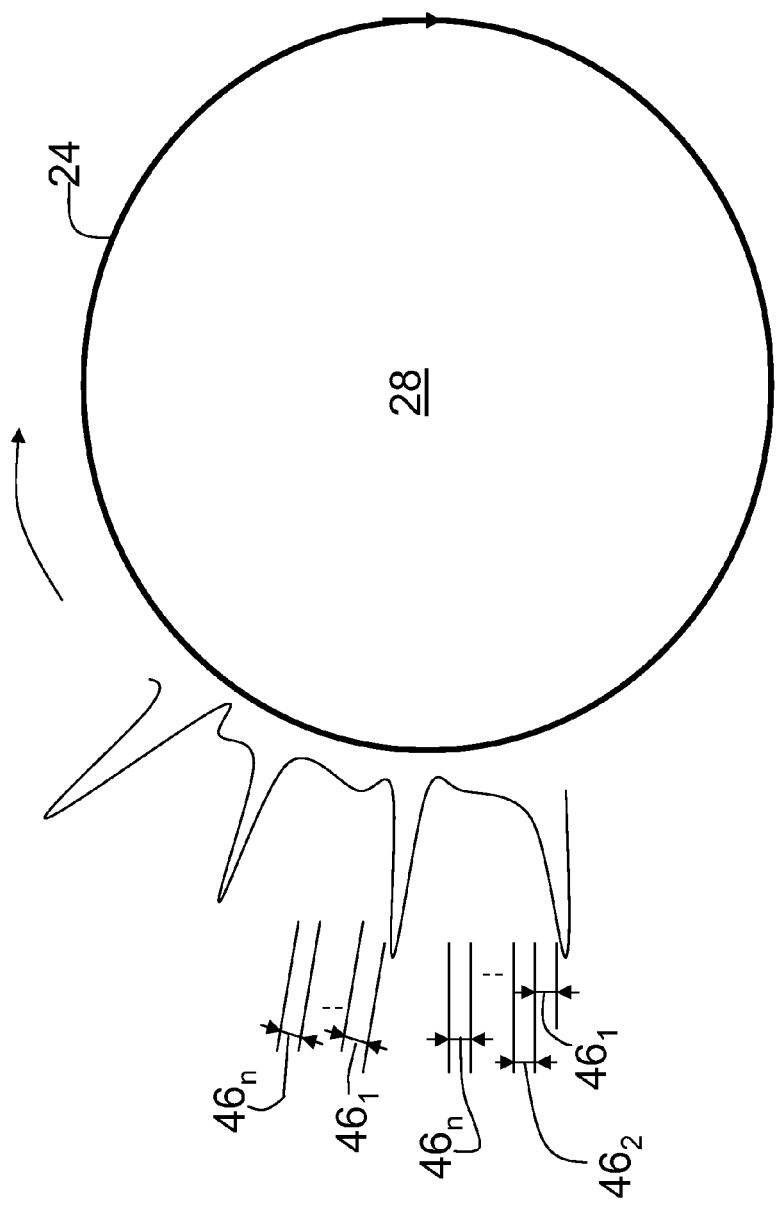

GATED CT WITH IRREGULAR SAMPLING FOR SLOW CT ACQUISITION

CROSS REFERENCE TO RELATED APPLICATIONS

This application claims the benefit of U.S. provisional application Ser. No. 60/820,809 filed Jul. 31, 2006, which is incorporated herein by reference.

The present application relates to the diagnostic imaging arts. It finds particular application in conjunction with the Single Photon Emission Tomography (SPECT) systems with attenuation compensation and will be described with particular reference thereto. It will be appreciated that the invention is also applicable to other imaging systems such as Positron Emission Tomography systems (PET), Computed Tomography systems (CT), and the like.

Nuclear medicine imaging employs a source of radioactivity to image a patient to obtain diagnostic information in a functional or molecular level. Typically, one or more radiopharmaceuticals are injected into the patient. Radiopharmaceutical compound contains a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

In gated cardiac imaging, a characteristic point in each cardiac cycle triggers the collection of data. This enables the acquired data to be sorted by cardiac phase. For example, after the triggering time, the interval until the next triggering time is divided up into several equal segments, e.g. 16 segments per cardiac cycle. Over a number of preselected cardiac cycles, complete data sets are acquired for each of the plurality of cardiac phases. Data from the same cardiac phase in each of the plurality of cycles is combined based on one of the known algorithms to obtain enough statistics.

In clinical studies, generally, the radiations inside a subject cannot reach the detectors with equal probabilities due to the attenuation effect, which is determined by varying absorption characteristics of the patient's anatomy. Hence, an attenuation map (transmission map) either generated by a transmission radiation source or a CT image is used to provide additional attenuation information to correct the emission data. However, currently, a gated emission study usually has no attenuation correction, which affects the accurate diagnosis.

One solution is to provide a common attenuation map for all phases of the cardiac cycle. For example, transmission radiation of a different energy than the emission can be collected during the SPECT sequence. The transmission data collected over all phases of the cardiac cycle can be reconstructed into an attenuation map with a resolution comparable to the SPECT image. For a single source transmission method, however, there is statistically insufficient transmission data to be gated and reconstructed into attenuation maps of sufficient resolution for each cardiac phase. Because dense tissue in and around the heart moves during the cardiac cycle, the attenuation map generated from data collected over the full cardiac cycle is blurred and might cause inaccuracies for SPECT data from the individual cardiac phases. For example, about 20-30% of cardiac studies in current SPECT/CT systems suffer from this problem.

The present application provides new and improved methods and apparatuses which overcome the above-referenced problems and others.

In accordance with one aspect, an imaging system is disclosed. A physiological parameter monitor monitors a cyclic physiological parameter and generates a cyclic parameter phase indicative signal. A radiation system is disposed adjacent an examination region to generate transmission radiation data and emission radiation data. First and second sorting devices sort corresponding transmission and emission radiation data into transmission radiation data sets and emission radiation data sets corresponding to each of a plurality of the cyclic parameter phases. A data processor reconstructs attenuation maps from the transmission data for each of the plurality of cyclic parameter phases. An image processor corrects the emission radiation data of each cyclic parameter phase with the attenuation map of the same cyclic parameter phase and reconstructs the attenuation corrected emission data sets into an image representation for each cyclic parameter phase.

In accordance with another aspect, an imaging method is disclosed. A cyclic physiological parameter is monitored. A cyclic parameter phase indicative signal is generated. A radiation system is disposed adjacent an examination region to generate transmission radiation data and emission radiation data. Corresponding transmission and emission radiation data are sorted into transmission radiation data sets and emission radiation data sets corresponding to each of a plurality of the cyclic parameter phases. Attenuation maps are reconstructed from the transmission data for each of the plurality of cyclic parameter phases. The emission radiation data of each cyclic parameter phase are corrected with the attenuation map of the same cyclic parameter phase. The attenuation corrected emission data sets are reconstructed into an image representation for each cyclic parameter phase.

In accordance with another aspect, a diagnostic imaging system is disclosed. A CT scanner includes a rotating gantry that rotates around an examination region, an x-ray source that irradiates the examination region with x-rays, and a radiation detector that detects x-rays that have transversed the examination region. A nuclear scanner detects emission radiation from a region of a subject in an examination region. A cardiac monitor monitors a cardiac cycle of the subject. At least one sorting device sorts x-ray radiation data from the CT scanner into a set of transmission data for each of a plurality of preselected cardiac phases collected over a plurality of cardiac cycles and sorts the emission radiation data into a set of emission data for each of the plurality of preselected cardiac phases collected over a plurality of cardiac cycles. At least one data processor reconstructs the transmission data sets into an attenuation map for each of the plurality of preselected cardiac phases, corrects emission data from the emission data set for each of the preselected cardiac phases with the attenuation map corresponding to the same one of the preselected cardiac phases and reconstructs an image representation from the attenuation corrected emission data for each of the preselected cardiac phases.

One advantage is that the attenuation maps are determined for each individual cardiac phase for better accuracy.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 2 is a diagrammatic illustration of a rotating gantry with the transmission radiation data sets being acquired at each cardiac phase.

Figure 1:
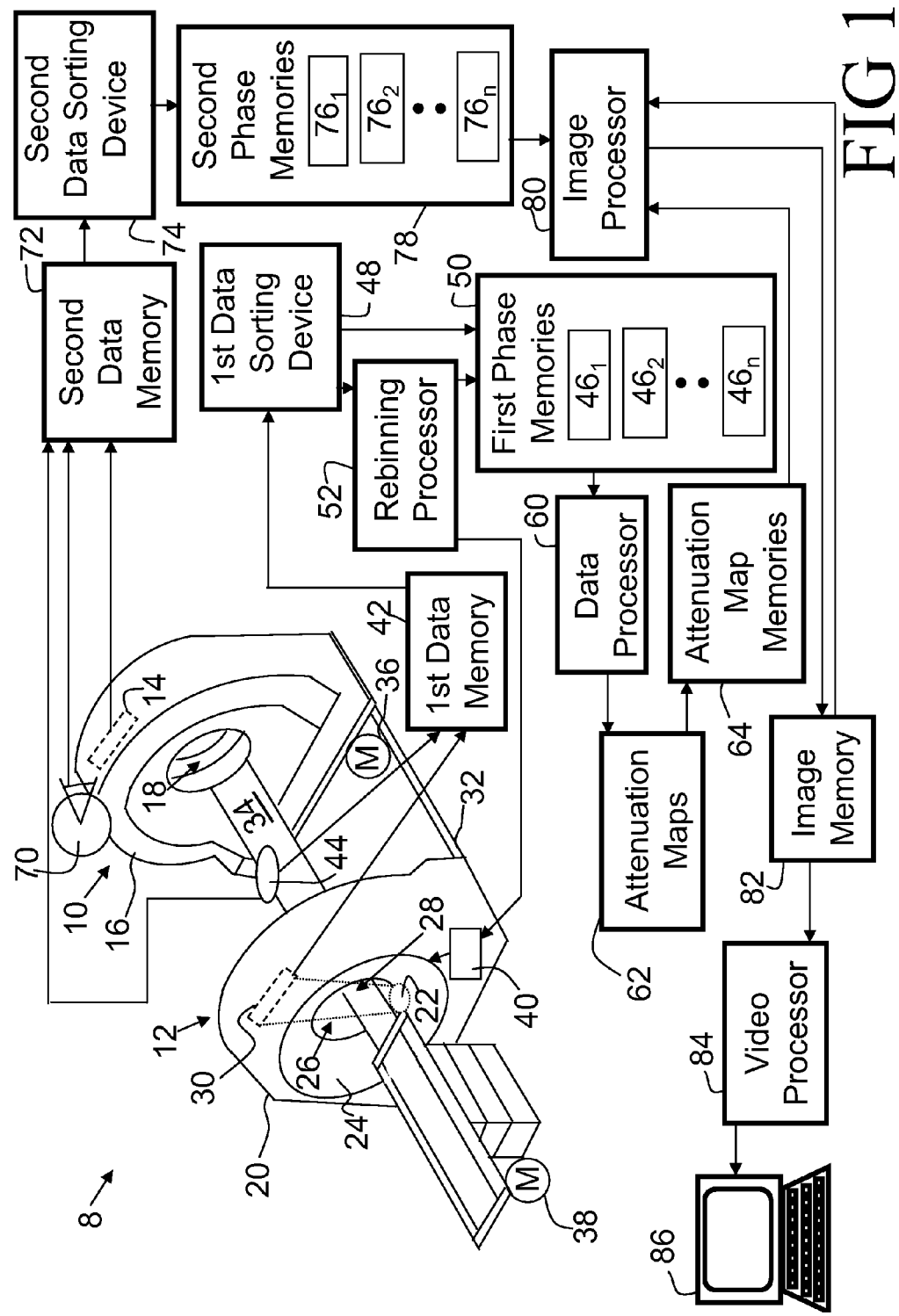
FIG. 1 is a diagrammatic illustration of an imaging system.

With reference to FIG. 1, an imaging system 8 includes a nuclear imaging system 10 such as a SPECT or PET scanner and a CT scanner 12. More specifically, one or more nuclear detection heads 14 are carried by a rotatable gantry 16 to detect radiation events emanating from a region of interest or examination region 18. Each detection head 14 includes two-dimensional arrays of detector elements, such as a scintillator and an array of light sensitive elements, e.g. photomultiplier tubes, photodiodes, and the like. Direct gamma-ray to electrical converters, such as CZT elements, are also contemplated. Alternatively, particularly in a PET scanner, the examination region is typically surrounded by a ring of stationary detector heads. Each head 14 includes circuitry for converting each radiation response into a digital signal indicative of its location (x, y) on the detector face, its energy (z), angular position of the head, and detection time. The location of an event on the detector is resolved and/or determined in a two dimensional (2D) Cartesian coordinate system with nominally termed x and y coordinates. However, other coordinate systems are contemplated. In the SPECT scanner, a collimator controls the direction and angular spread, from which each element of the detector can receive radiation, i.e., the detector can receive radiation only along known rays. Thus, the determined location on the detector at which radiation is detected and the angular position of the head 14 define the nominal ray along which each radiation event occurred.

As the emission data normally contains inaccuracies caused by varying absorption characteristics of the patient's anatomy (i.e. attenuation effect), in one embodiment, the CT scanner 12 is utilized to provide additional attenuation information to correct the emission data. The CT scanner 12 includes a non-rotating gantry 20. A radiation source or sources 22, such as an x-ray tube, is mounted to a rotatable gantry 24. A bore 26 defines an examination region 28 of the CT scanner 12. A non-bore system, such as L-shape, arc, and other are also contemplated. An array of radiation detectors or a radiation detector 30 is disposed on the rotatable gantry to receive radiation from the x-ray tube 22 after the x-rays transverse the examination region 28. Alternatively, a gamma radiation source is used to provide a source of the transmission radiation. In one embodiment, the radiation detector 30 includes flat panel detectors.

Tracks 32 extend in parallel to a longitudinal axis of a subject support or couch 34, thus enabling the SPECT scanner 10 and CT scanner 12 to form a closed system. A moving means 36, such as a motor and a drive, is provided to move the SPECT scanner 10 in and out of the closed position. A couch moving means 38, such as a motor and a drive, provides a longitudinal movement and vertical adjustment of the couch 34 in the examination regions 18, 28. It is contemplated that the relative positions (front or back) of CT and SPECT scanners depend on the needs of a particular design or application.

In one embodiment, the nuclear imaging system 10 and the CT scanner employ a common gantry. In such system, the detection is performed simultaneously or interleaved.

With continuing reference to FIG. 1, as the rotatable gantry 24 of the CT scanner 12 rotates at a constant speed, a subject or patient, which is positioned on a couch or subject support table 34, is moved into an examination region 28, where the CT image is taken. In one embodiment, a gantry motion control 40 sets a rotational speed w of the rotatable CT gantry low, for example, from about 0.5 RPM to about 6 RPM. The drive 38 advances and/or retracts the subject support 34 to achieve the desired positioning of the subject within the examination region 28. The x-ray radiation data collected by the detector 30 is stored in a first or CT data memory 42.

A cycle monitor 44 monitors prespecified biological cycles of the patient. In one embodiment, the cycle monitor 44 monitors the patient's heart. More specifically, via leads attached to the patient, an ECG monitor acquires ECG data from the patient. Alternately, the heart may be monitored via another device such as, e.g., an echo heart monitor, an ultrasound heart monitor, a heart sound monitor, a pulse oximeter, etc. In another embodiment, the cycle monitor 44 monitors patient's respiratory cycle. More specifically, a respiratory sensing belt is connected with a balanced bridge type pressure transducer which produces an electrical signal that varies in amplitude with the respiratory cycle. Commonly, the cardiac cycle is from about a half of a second to about one second in length and the respiratory cycle is from about five to about ten seconds in length.

With continuing reference to FIG. 1 and further reference to FIG. 2, as the cycle monitor 44 detects phase points selected in each R-R interval by the clinician or user according to the motion characteristics of the heart, time since an R-wave and the required diagnostic information, and the like, the x-ray source 22 is turned ON at each denoted phase point and one or more sets of CT data is collected during each phase $46_1, 46_2, \ldots, 46_n$. Alternatively, the CT data can be collected continuously with each data set being marked to indicate the cardiac phase in which it was collected.

A first or CT sorting device, processor, mechanism or other means 48 sorts the attenuation data into data sets collected during each of the selected cardiac phases, i.e. cardiac phase specific data sets which are stored in a first phase memories 50. In one embodiment, a re-binning processor 52 re-bins the cardiac phase specific data from cone to parallel beam geometry into a set of parallel views. Particularly for cardiac phases defined by a short temporal window, the data for one cardiac phase corresponds to data collected over short arc segments in one or more rotations and cardiac cycles. Because the rotatable gantry 24 is set at a slow motion, the data collected in each of the arc segments is adequate to reconstruct an image. For example, if the rotatable gantry 24 speed is set at 0.5 RPM, for a patient with a regular heartbeat of 75 beats/minute, after the full 360° revolution, 150 sets of CT data are generated for each cardiac phase.

As the re-binning processor 52 re-bins the collected data, the re-binning processor 52 monitors the data for a bad beat. If a bad heart beat is detected, any data collected during that bad beat is discarded. If an excessive number of bad beats are detected, it may be appropriate to extend the number of rotations to rescan a segment with most of the bad beats or the 180° opposite segment. Alternatively, the gantry motion control 40 can retrack partial rotation (move the detectors back to the point where a bad beat is detected) as soon as a bad beat is detected to eliminate big sampling gap in the projection data.

A data processor 60 reconstructs a 3D transmission radiation image or attenuation maps 62 for each individual cardiac phase. The CT data in each phase is sparsely sampled and, typically, not uniformly sampled due to the non-uniform heartbeat. The data processor 60 reconstructs the CT data using, for example, a reconstruction technique which models the uneven data sampling pattern. As another example, interpolation and normalization techniques can be utilized. As yet another example, data from similar cardiac cycles can be used. From the each attenuation map 62, an array of attenuation factors for each phase is determined and stored in a phase attenuation map memories 64. Each voxel value stored in the attenuation map memories 64 is indicative of attenuation of radiation by tissue in a corresponding volume, e.g. a corresponding phase of a cardiac cycle. SPECT images typically have lower resolution than the CT images. Reconstructing the attenuation map with a resolution comparable with the SPECT resolution helps compensate for the sparsety of data.

With continuing reference to FIG. 1, the subject support table 34 with the subject is moved into the SPECT examination region 18 to position the subject to take the SPECT image. Typically, prior to the examination, the subject to be imaged is injected with one or more radiopharmaceuticals or radioisotopes. Few examples of such isotopes are Tc-99m, Ga-67, and In-111. The presence of the radiopharmaceuticals within the object produces emission radiation from the object. Data collection for a SPECT image is typically on the order of 5-40 minutes. During the data collection, the SPECT detector heads 14 are typically rotated in steps or continuously around the examination region 18 to collect the projection emission data at a multiplicity of projection directions. In one embodiment, the heads are rotated over an arc of 360° divided by the number of heads. The projection emission data, e.g. the location (x, y), energy (z), and an angular position (θ) of each detection head 14 around the examination region 18 (e.g., obtained from an angular position resolver 70) are stored in a second or emission data memory 72. The cycle monitor 44 monitors the patient's cardiac cycle and detects phase points typically relative to the R-wave of each cycle, i.e. in each R-R interval. The emission radiation data is collected during each selected cardiac phase $76_1$, $76_2$, . . . , $76_n$. A second or emission data sorting device, processor, mechanism or other means 64 sorts the emission radiation data into data sets collected during each of the selected cardiac phases, i.e. cardiac phase specific data sets which are stored in corresponding second phase memories 78.

In one embodiment, one or more of the emission data gates and transmission data gates differ from each other, i.e. there can be grouping.

An image processor, algorithm, mechanism or other means 80 iteratively reconstructs a 3D image representation in an image memory 82. For each ray, along which emission data is received, the image processor 80 calculates a corresponding ray through a corresponding attenuation map array stored in the phase attenuation map memories 64. Each ray of the emission data of each individual cardiac phase is weighted or corrected in accordance with the attenuation factors.

A video processor 84 retrieves slices, projections, 3D renderings, and other information from the image memory and appropriately formats an image representation for display on a monitor or monitors 86. Any state of the art display software can be used. Of course, a printer or other output device may also be used to present data in a convenient format.

In one embodiment, the user selects the phases via, for example, a graphical user interface integrated with the monitor 86 or any other appropriate personal computer, PDA and the like.

In one embodiment, the images are organized by the imaging system at different times and at different positions along a scanner axis. For example, a respiratory marker, which is coupled with respiration of the imaging subject, moves with the respiration. The marker is arranged to intersect the images acquired at different times and at different positions along the scanner axis and is detectable as a marker feature in the images so the positions of the marker features in the images can be determined. In this manner, the respiratory monitoring data is embedded directly with the imaging data, avoiding the need to store and temporally synchronize separate monitoring and imaging data sets. The synchronization is automatically achieved.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system comprising:
    a physiological parameter monitor which monitors a cyclic physiological parameter of a subject in an examination region and generates a cyclic parameter phase indicative signal;
    a rotatable gantry which rotates around the examination region;
    a radiation source mounted on the rotatable gantry;
    a gantry control which controls a rotational speed of the rotatable gantry, the rotational speed being from about 0.5 RPM to about 6 RPM;
    a radiation detector which detects radiation from the radiation source that has transversed the examination region as the gantry rotates and which detects emission radiation emitted from the subject to generate transmission radiation data and emission radiation data;
    first and second sorting devices which sort corresponding transmission and emission radiation data into transmission radiation data sets and emission radiation data sets corresponding to each of a plurality of the cyclic parameter phases indicated by the cyclic phase indicative signal;
    a data processor which reconstructs attenuation maps from the transmission data for each of the plurality of cyclic parameter phases; and
    an image processor which corrects the emission radiation data of each cyclic parameter phase with the attenuation map of the same cyclic parameter phase and reconstructs the attenuation corrected emission data sets into an image representation for each cyclic parameter phase.

2. The system as set forth in claim 1, wherein the radiation source includes:
    a cone beam x-ray radiation source which generates a cone beam of x-ray radiation which transverses the examination region.

3. The system as set forth in claim 2, wherein the gantry control rotates the rotatable gantry at a substantially slow speed so that there are at least 5 repetitions of the cyclic parameter phase per revolution.

4. The system as set forth in claim 2, further including:
    a gating system for gating the x-ray beam on/off with cyclic parameter phase to collect data in each cyclic parameter phase of each cycle.

5. The system as set forth in claim 1, wherein the data processor reconstructs an attenuation map for each cyclic parameter phase from transmission data collected over a single rotation of the rotatable gantry.

6. The system as set forth in claim 1, wherein the physiological parameter monitor monitors cardiac cycles of an imaged subject, during which cardiac cycles the transmission and emission radiation data are sorted into corresponding cardiac cyclic phases.

7. The system as set forth in claim 6, wherein the cardiac cycles are selectable by a user on a graphical user interface.

8. The system as set forth in claim 1, wherein the transmission data from which the data processor reconstructs the attenuation maps is non-uniformly angularly sampled.

9. An imaging method comprising:
controlling a rotational speed of a rotatable gantry, the rotational speed being from about 0.5 RPM to about 6 RPM;
emanating radiation with a radiation source mounted on the rotatable gantry;
detecting radiation from the radiation source that has transversed the examination region as the gantry rotates;
monitoring a cyclic physiological parameter;
generating a cyclic parameter phase indicative signal;
generating transmission radiation data and emission radiation data;
sorting corresponding transmission and emission radiation data into transmission radiation data sets and emission radiation data sets corresponding to each of a plurality of the cyclic parameter phases;
reconstructing attenuation maps from the transmission radiation data for each of the plurality of cyclic parameter phases;
correcting the emission radiation data of each cyclic parameter phase with the attenuation map of the same cyclic parameter phase; and
reconstructing the attenuation corrected emission data sets into an image representation for each cyclic parameter phase.

10. The method as set forth in claim 9, further including:
acquiring projection data sets within a plurality of temporal windows corresponding to the cyclic parameter phases, including:
transversing the examination region with a cone beam x-ray radiation,
detecting the x-ray radiation after it passes through the examination region, and
converting the x-ray radiation into the transmission radiation data.

11. The method as set forth in claim 10, further including:
rotating the rotatable gantry at a substantially slow speed so that there are at least 5 repetitions of the cyclic parameter phase per revolution.

12. The method as set forth in claim 10, further including:
gating the radiation source on/off with the cyclic parameter phase to collect data in each cyclic parameter phase of each cycle.

13. The method as set forth in claim 9, wherein the step of reconstructing includes:
reconstructing an attenuation map for each cyclic parameter phase from transmission radiation data collected over a single rotation of the rotatable gantry.

14. A diagnostic scanner for performing the steps of claim 9.

15. A diagnostic imaging system including:
a CT scanner including:
a rotating gantry that rotates around an examination region,
an x-ray source that irradiates the examination region with x-rays, and
a radiation detector that detects x-rays that have transversed the examination region;
a nuclear scanner which detects emission radiation from a region of a subject in an examination region;
a cardiac monitor which monitors a cardiac cycle of the subject;
at least one sorting device which sorts x-ray radiation data from the CT scanner into a set of transmission data for each of a plurality of preselected cardiac phases collected over a plurality of cardiac cycles and which sorts the emission radiation data into a set of emission data for each of the plurality of preselected cardiac phases collected over a plurality of cardiac cycles;
at least one data processor which reconstructs the transmission data sets into an attenuation map for each of the plurality of preselected cardiac phases, corrects emission data from the emission data set for each of the preselected cardiac phases with the attenuation map corresponding to the same one of the preselected cardiac phases and reconstructs an image representation from the attenuation corrected emission data for each of the preselected cardiac phases; and
wherein the rotating gantry rotates sufficiently slowly that transmission data is acquired during at least 8 cardiac cycles per revolution.

16. The system as set forth in claim 15, further including:
a processor which monitors the x-ray radiation data for an irregular heart beat and discards data acquired during the irregular heart beat.

17. The system as set forth in claim 16, wherein x-ray radiation data is retaken to replace data discarded in response to the irregular heart beat.

18. The system as set forth in claim 15, further including:
a gating system for gating the CT scanner to generate data in each of the preselected cardiac phases in each of a plurality of cardiac cycles.

19. The system as set forth in claim 15, wherein the nuclear scanner includes at least one of a SPECT and PET scanner.

20. A method of generating nuclear medicine images, comprising:
receiving emission image data and non-uniformly angularly sampling transmission image data, the transmission image data being sampled over 360° in 0.5-6 minutes;
sorting the non-uniformly angularly sampled transmission data into a selectable number of cardiac phases, the transmission data in at least one of the cardiac phases being non-uniformly angularly sampled;
sorting the emission data into the selectable number of cardiac phases;
generating attenuation correction maps from the transmission image data for each of the cardiac phases using at least one of (1) a reconstruction technique which models the non-uniformly angularly sampling and (2) interpolation;
correcting the emission image data in each cardiac phase with a corresponding gated attenuation correction map;
reconstructing the attenuation corrected emission data into images; and
displaying the images on a display device.

21. The method as set forth in claim 20, wherein generating the attenuation correction maps includes using interpolation.

* * * * *